(12) United States Patent
Sasanuma et al.

(10) Patent No.: US 7,574,900 B2
(45) Date of Patent: Aug. 18, 2009

(54) LIQUID STATE DETECTION SENSOR

(75) Inventors: Takeo Sasanuma, Aichi (JP); Yoshikuni Sato, Nagoya (JP); Shunsuke Tamura, Komaki (JP); Shinji Kumazawa, Nagoya (JP); Hisashi Sasaki, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 467 days.

(21) Appl. No.: 11/482,026

(22) Filed: Jul. 7, 2006

(65) Prior Publication Data

US 2007/0006639 A1    Jan. 11, 2007

(30) Foreign Application Priority Data

Jul. 8, 2005    (JP)    ............... 2005-200808
Sep. 26, 2005    (JP)    ............... 2005-277776

(51) Int. Cl.
*G01N 25/00*    (2006.01)
(52) U.S. Cl. ..................... 73/61.46; 73/61.76
(58) Field of Classification Search ............... 73/61.46, 73/61.76; 374/16
See application file for complete search history.

(56) References Cited

U.S. PATENT DOCUMENTS

| | | | |
|---|---|---|---|
| 4,762,427 A * | 8/1988 | Hori et al. ............ | 374/141 |
| 6,509,553 B2 * | 1/2003 | Golan et al. ............ | 219/505 |
| 2007/0054409 A1 * | 3/2007 | Inoue et al. ............ | 436/108 |
| 2007/0110618 A1 * | 5/2007 | Sasanuma et al. ....... | 422/68.1 |
| 2007/0113625 A1 * | 5/2007 | Sasanuma et al. ....... | 73/61.46 |
| 2007/0125663 A1 * | 6/2007 | Sasanuma et al. ....... | 205/777 |

FOREIGN PATENT DOCUMENTS

| | | |
|---|---|---|
| CN | 2296006 Y | 10/1998 |
| EP | 1 669 743 A1 | 6/2006 |
| JP | 5-72099 A | 3/1993 |
| JP | 2005-84026 A | 3/2005 |

OTHER PUBLICATIONS

Grob, Bernard. Basic Electronics. 6th Edition (New York, McGraw-Hill) 1989. p. 62.*

* cited by examiner

*Primary Examiner*—Hezron Williams
*Assistant Examiner*—Nathaniel Kolb
(74) *Attorney, Agent, or Firm*—Sughrue Mion, PLLC

(57) ABSTRACT

A liquid state detection sensor in which temperature information of a urea aqueous solution is obtained on the basis of a voltage value acquired after the start of energization of a heating resistor corresponding to a resistance value of the heating resistor (S1-S6). Damage to the heating resistor is prevented by suspending the energization if the thus-obtained temperature is lower than or equal to the freezing point (S7: yes and S8). If the temperature is higher than the freezing point (S7: no), a voltage value corresponding to a resistance of the heating resistor after a lapse of 700 ms (S10 and S11) and a urea concentration of the urea aqueous solution are determined from a difference ΔV from the previously acquired voltage value. A more accurate urea concentration can be detected by making a correction using the previously obtained temperature information of the urea aqueous solution (S13-S18).

8 Claims, 9 Drawing Sheets

LIQUID STATE DETECTION SENSOR

BACKGROUND OF THE INVENTION

1. Field of the Invention

The present invention relates to a liquid state detection sensor for detecting the temperature and the concentration of a particular component of a liquid contained in a liquid container.

2. Description of the Related Art

In recent years, NOx selective catalytic reduction (SCR) has come to be employed in exhaust emission control apparatus which reduce nitrogen oxides (NOx) emitted from diesel vehicles, for example, into harmless gases. A urea aqueous solution is used as a reducing agent for that purpose. It is known that the use of a urea aqueous solution having a urea concentration of 32.5 wt % is appropriate for carrying out efficient chemical reduction. However, a urea aqueous solution contained in a urea solution tank installed in an automobile is stored under severe environmental conditions and its urea concentration may vary with age, for example. Further, another kind of liquid (e.g., light oil) or water may erroneously be poured into the urea solution tank. Therefore, so as, to manage the urea concentration of a urea aqueous solution, the urea concentration is detected by attaching a urea concentration sensor to the urea solution tank.

Incidentally, the thermal conductivity of a urea aqueous solution depends on its urea concentration. Therefore, a concentration sensor (in which the temperature of a heating body that generates heat due to current flowing therethrough is measured using a temperature sensing element) may be configured in which heat conduction from the heating body to the temperature sensing element is influenced by a surrounding liquid. In this concentration sensor, a measured temperature of the heating body reflects the concentration of the liquid. Therefore, the urea concentration of a urea aqueous solution can be detected according to a relationship between the urea concentration and the temperature variation of the heating body. This is done by energizing the heating body for a prescribed time and measuring the temperature of the heating body with the temperature sensing element before and after energization (refer to JP-A-2005-84026, for example). The relationship between the urea concentration and the temperature variation of the heating body also depends on the (initial) liquid temperature. Therefore, in JP-A-2005-84026, the urea concentration of a urea aqueous solution is detected by measuring both the temperature of the urea aqueous solution using a temperature sensing element different from the one used to measure the temperature variation of the heating body. JP-A-2005-84026 proposes to issue an alarm on the basis of output information of the separate temperature sensing element, if the temperature of a urea aqueous solution is detected as being as low as its freezing point.

3. Problems to be Solved by the Invention

However, the concentration sensor of JP-A-2005-84026, whose concentration sensing portion is provided with a temperature sensing element separate from that accompanying the heating body, is disadvantageous in that the concentration sensor is large and the circuitry for the concentration detection has a complex configuration.

Furthermore, a urea aqueous solution contained in the urea solution tank may freeze in colder climates. In such a case, the urea aqueous solution cannot be jetted onto the catalyst, and hence it is necessary to wait until it melts. As described above, although JP-A-2005-84026 issues an alarm which notifies of freezing of a urea aqueous solution using the temperature sensing element that is separate from the one accompanying the heating body, it does not refer to any processing to be performed on the heating body when the urea aqueous solution is frozen. The concentration sensing portion may be damaged if the step of detecting urea concentration by energizing the heating body for a prescribed time is repeated while the urea aqueous solution is frozen. More specifically, if the heating body is energized for a prescribed time in a state such that the urea aqueous solution is frozen, part of the urea aqueous solution around the concentration sensing portion melts due to the generated heat. However, the melted portion of the urea aqueous solution is frozen again if most of the urea aqueous solution remains frozen, and the concentration sensing portion may be damaged due to pressure caused by freezing expansion.

SUMMARY OF THE INVENTION

The present invention has been made to solve the above-noted problems of the prior art, and an object of the invention is therefore to provide a liquid state detection sensor capable of detecting temperature and the concentration of a liquid using a single device having a heating resistor, as well as preventing the device from becoming damaged when the liquid is frozen.

To attain the above object, the liquid state detection sensor according to a first aspect of the invention is a liquid state detection sensor for detecting the state of a liquid contained in a liquid container, comprising a liquid condition detecting element that is to be placed in the liquid container and having a heating resistor which generates heat when a current is passed therethrough; an energizing unit for energizing the heating resistor for a prescribed detection period; a first corresponding value acquiring unit for acquiring, in the detection period, a first corresponding value which corresponds to a first resistance value of the heating resistor; a temperature information acquiring unit for determining a temperature of the liquid based on the first corresponding value; a second corresponding value acquiring unit for acquiring, after a lapse of the detection period, a second corresponding value which corresponds to a second resistance value of the heating resistor; a difference calculating unit for determining a difference between the second corresponding value and the first corresponding value; and a concentration acquiring unit for determining a concentration of a particular component of the liquid based on the difference between the second and first corresponding values, and in a further preferred embodiment, based on this difference and the temperature of the liquid.

In the liquid state detection sensor according to this aspect of the invention, the liquid condition detecting element includes a heating resistor having a resistance which varies as its temperature increases. Before the heating resistor is energized, the temperature of the heating resistor is approximately equal to the temperature of the portion of liquid surrounding it. That is, shortly after the start of energization of the heating resistor, the resistance of the heating resistor strongly correlates with the temperature of the surrounding portion of the liquid. This is because the influence of its heating on its resistance is still small. Based thereon, in this aspect of the invention, the temperature of a surrounding portion of the liquid is detected based on a first corresponding value, acquired only a short time after the start of energizing the heating resistor, and which corresponds to a first resistance value.

The thermal conductivity of a liquid depends on the concentration of the particular component of the liquid. Therefore, when liquid portions around the heating resistor of differing concentrations are heated for a prescribed time by the heating resistor, the respective liquids are expected to exhibit different temperature increase rates. Based thereon, in this aspect of the invention, the concentration of the particular component of a liquid is detected by energizing the heating resistor for a prescribed time and detecting a temperature increase rate of the heating resistor based on the difference between a first corresponding value (i.e., a first resistance value of the heating resistor acquired only a short time after the start of energization) and a second corresponding value (i.e., a second resistance value of the heating resistor acquired after the heating resistor has been energized) for a detection period.

Incidentally, even if the concentration of the particular component of a liquid remains the same, the temperature increase rate of the heating resistor (i.e., the difference between the above second and the first corresponding values) varies with the (initial) temperature of the liquid. That is, the temperature increase rate of the heating resistor depends on the temperature of the liquid. In view of the above, in this aspect of the invention, in detecting the concentration of the particular component of the liquid in the above-described manner, the difference between the above second and first corresponding values is preferably corrected by taking into account the temperature of the liquid as determined based on the first corresponding value acquired only a short time after the start of energization of the heating resistor. This measure makes it possible to correctly detect the concentration of the particular component of a liquid independent of its temperature. Alternatively, for example, the difference may be corrected by taking into account the temperature of a liquid by determining, in advance, relationships between the difference in second and first corresponding values and the liquid temperature for reference liquids having prescribed concentrations, and storing a table (map) or calculation formulae produced on the basis of the above relationships in the concentration acquiring unit.

Further, in this aspect of the invention, the temperature detection and the concentration detection can be performed on a liquid using a single liquid condition detecting element (also is called a directly heated liquid condition detecting element) having a heating resistor which functions as both a heating body for heating a liquid and a temperature sensing element. This enables miniaturization of the liquid state detection sensor, and can simplify the structure and the detection circuitry.

To attain the above object, the liquid state detection sensor according to a second aspect of the invention further comprises a freezing judging unit for judging, in the detection period, on the basis of the temperature determined by the temperature information acquiring unit, whether the liquid is frozen; and an energization suspending unit for suspending the energization of the heating resistor by the energizing unit if the freezing judging unit judges that the liquid is frozen.

In this aspect of the invention, since the temperature detection and the concentration detection are performed by the liquid condition detecting element having such a structure, it is possible to detect whether a liquid is frozen by acquiring a temperature of the liquid when first energizing the heating resistor. Concentration detection is then performed by energizing the heating resistor for a prescribed detection period after the temperature detection. If the liquid is frozen, only a portion of the liquid, around the liquid condition detecting element melts due to heat generated by the heating resistor. However, the melted portion of the liquid is frozen again if most of the liquid remains frozen. The liquid condition detecting element may be damaged by pressure due to freezing expansion.

In view of the above, in this aspect of the invention, a judgment as to whether a liquid is frozen is based on the temperature information acquired by the temperature information acquiring unit only a short time after the start of energization of the heating resistor and prior to energizing the heating resistor for the prescribed detection period. If the liquid is judged to be frozen, further energization of the heating resistor by the energizing unit is forcibly prohibited. Even if a liquid is frozen, such measure prevents damage to the liquid condition detecting element due to pressure caused by re-freezing expansion. A highly reliable liquid state detection sensor can thus be provided.

The first corresponding value of this aspect of the invention may be any value corresponding to the first resistance value of the heating resistor. Specific examples of the first corresponding value are a voltage value, a current value, and a converted temperature value. Likewise, the second corresponding value of this aspect of the invention may be any value corresponding to the second resistance value of the heating resistor. However, since it is necessary to determine the difference between the second corresponding value and the first corresponding value, if the first corresponding value is a voltage value, for example, the second corresponding value should also be a voltage value. Further, where a third corresponding value is acquired as described below, it becomes necessary to determine the difference between the third corresponding value and the first corresponding value. If the first corresponding value is a voltage value, for example, the third corresponding value should also be a voltage value.

Further, in this aspect of the invention, the timing of acquisition of a first corresponding value by the first corresponding value acquiring unit may be only a short time after the start of energization of the heating resistor, that is, in a period when the temperature of the heating resistor itself is approximately equal to the temperature of the surrounding portion of the liquid. More specifically, it is satisfactory to acquire a first corresponding value within 100 ms of the start of energization of the heating resistor. The current flowing through the heating resistor tends to be unstable in a certain period after the start of energization of the heating resistor. Therefore, it is preferable to acquire a first corresponding value when a time of 2 ms to 100 ms (even preferably, to 50 ms) has elapsed from the start of energization of the heating resistor.

The liquid state detection sensor according to the second aspect of the invention may be such that the freezing judging unit judges that the liquid is frozen if the determined temperature is lower than or equal to a freezing point of the liquid.

In the liquid states detection sensor according to this aspect of the invention, a frozen state of the liquid is detected by judging whether the temperature determined by the temperature information acquiring unit is lower than or equal to the freezing point of the liquid. This makes it possible to quickly judge whether the liquid is frozen and to quickly suspend the energization of the heating resistor if it is judged that the liquid is frozen. This in turn prevents damage to the liquid condition detecting element due to pressure caused by re-freezing expansion even when the liquid is frozen again.

The liquid state detection sensor according to the second aspect of the invention may further comprise a third corresponding value acquiring unit for acquiring a third corresponding value which corresponds to a third resistance value of the heating resistor during the detection period and after acquisition of the first corresponding value. The freezing judging unit judges that the liquid is frozen if the detected temperature is lower than or equal to a preset threshold temperature, and an intermediate difference between the third corresponding value and the first corresponding value is in a prescribed magnitude relationship with a freezing judgment threshold value.

Incidentally, if the concentration of a liquid varies, the freezing temperature of the liquid varies accordingly. For example, where the liquid is a urea aqueous solution, the freezing temperature increases as the urea concentration decreases. Therefore, when the concentration of a particular component of the liquid has varied, merely comparing the temperature of the liquid with the preset freezing temperature may be insufficient to accurately judge whether the liquid is frozen.

In view of the above, in this aspect of the invention, whereas the temperature detected by the temperature information acquiring unit is compared with the preset threshold temperature, the intermediate difference, which is the difference between the third corresponding value and the first corresponding value, is compared with the freezing judging threshold value. The liquid is judged frozen if the detected temperature is lower than or equal to the preset threshold temperature, and the intermediate difference is in a prescribed magnitude relationship with the freezing judgment threshold value. Examples of the prescribed magnitude relationship are (1) (intermediate difference)<(freezing judgment threshold value) and (2) (intermediate difference)≦(freezing judgment threshold value).

Judging, as described above, whether the liquid is frozen in two steps, that is, by comparing the detected temperature with the threshold temperature and by comparing the intermediate difference with the freezing judgment threshold value, makes it possible to accurately judge whether the liquid is frozen even when the concentration of the particular component of the liquid has varied.

In the above liquid state detection sensor, preferably the energizing unit resumes energizing the heating resistor when a standby time has elapsed from the suspension of the energization of the heating resistor; and the liquid state detection sensor further comprises a standby time selecting unit for selecting, as the standby time, a first standby time if the energizing unit has energized the heating resistor for the detection period and a second standby time which is shorter than the first standby time if the energization suspending unit has suspended the energization of the heating resistor.

In the liquid state detection sensor according to this aspect of the invention, setting the standby time and waiting until the temperature of the heating resistor becomes approximately equal to the temperature of the surrounding portion of the liquid makes it possible to repeat correct temperature detection and particular component concentration detection on the liquid. If it is judged that the liquid is frozen, as described above the energization of the heating resistor is forcibly suspended. However, since the heating resistor has been energized for only a very short period of time, the heating resistor is exposed to an environment whose temperature is approximately the same as the temperature of the surrounding portion of the liquid. Consequently, in this aspect of the invention, the standby time to the next energization of the heating resistor is set shorter if the energization of the heating resistor is suspended because the liquid is judged to be frozen. This measure makes it possible to quickly repeat re-detection of a liquid temperature and hence to quickly judge that the liquid has melted. After the liquid has melted, its concentration can be quickly detected.

In the above liquid state detection sensor, preferably the liquid state detection sensor further comprises an abnormality judging unit for judging whether an abnormality has occurred in the liquid container using the difference determined by the difference calculating unit; and the concentration acquiring unit determines a concentration of the particular component of the liquid only if the abnormality judging unit judges that no abnormality has occurred with the determined difference.

As described above, if a difference that is acquired in detecting a concentration of the particular component of the liquid is outside the normal range, an abnormality is judged to have occurred. For example, this makes it possible to issue an alarm notifying of an abnormality such as, for example, the liquid in the liquid container is another kind of liquid such as light oil, or the liquid container is empty, or to restrict the operation of a device using the liquid. Further, since the concentration of the particular component of the liquid is determined on the basis of a difference in a normal range, the accuracy of the concentration detection can be increased.

In the above liquid states detection sensor, preferably the energizing unit causes a constant current to flow through the heating resistor; and the first and second corresponding value acquiring units acquire a voltage value as the first and second corresponding values, respectively.

Since the energizing unit is configured so as to cause a constant current to flow through the heating resistor, an accurate difference between the first and second corresponding values can be determined, while the circuit configuration is simplified. This makes it possible to provide an inexpensive liquid state detection sensor.

In the above liquid state detection sensor, the liquid condition detecting element is preferably a ceramic heater in which the heating resistor is buried in a ceramic base. Because the liquid condition detecting element comprises a ceramic heater that is superior in durability and corrosion resistance, it is possible to detect the temperature of a liquid and the concentration of its particular component stably over a long operating life.

In the above liquid state detection sensor, the liquid is preferably a urea aqueous solution and the particular component is urea. This makes it possible to detect the temperature and the urea concentration of a urea aqueous solution.

DESCRIPTION OF REFERENCE NUMERALS

Figure 1:
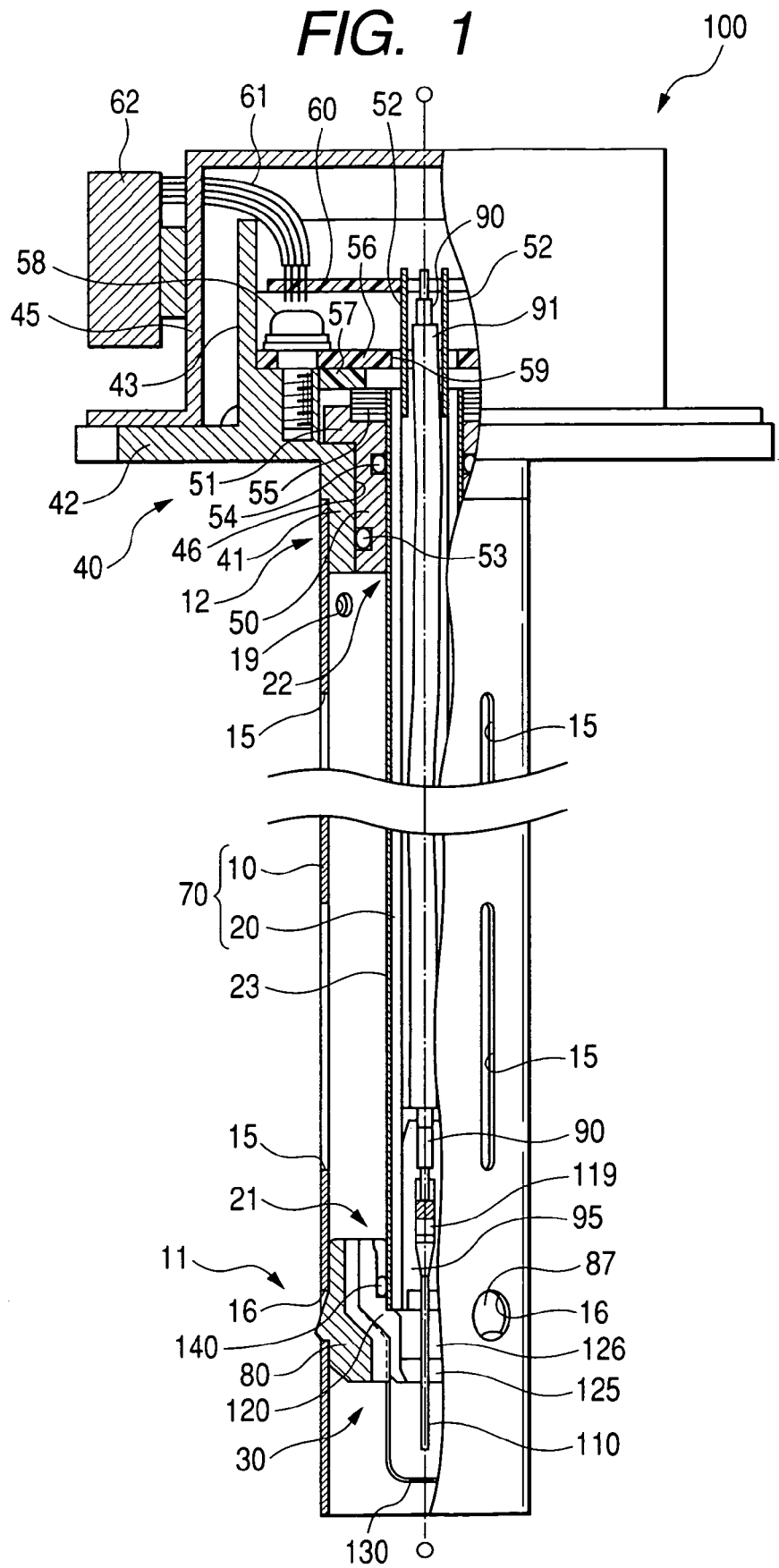
FIG. 1 is a partial sectional, longitudinal side view of a liquid state detection sensor 100.

Reference numerals used to identify various structural features in the drawings include the following.
98: Urea aqueous solution
100: Liquid states detection sensor
110: Ceramic heater
114: Heating resistor
220: Microcomputer
230: Differential amplifier circuit section
240: Constant current output section
221: CPU

DETAILED DESCRIPTION OF THE INVENTION

A liquid state detection sensor according to an embodiment of the invention will be hereinafter described with reference to the drawings. However, the present invention should not be construed as being limited thereto.

Figure 2:
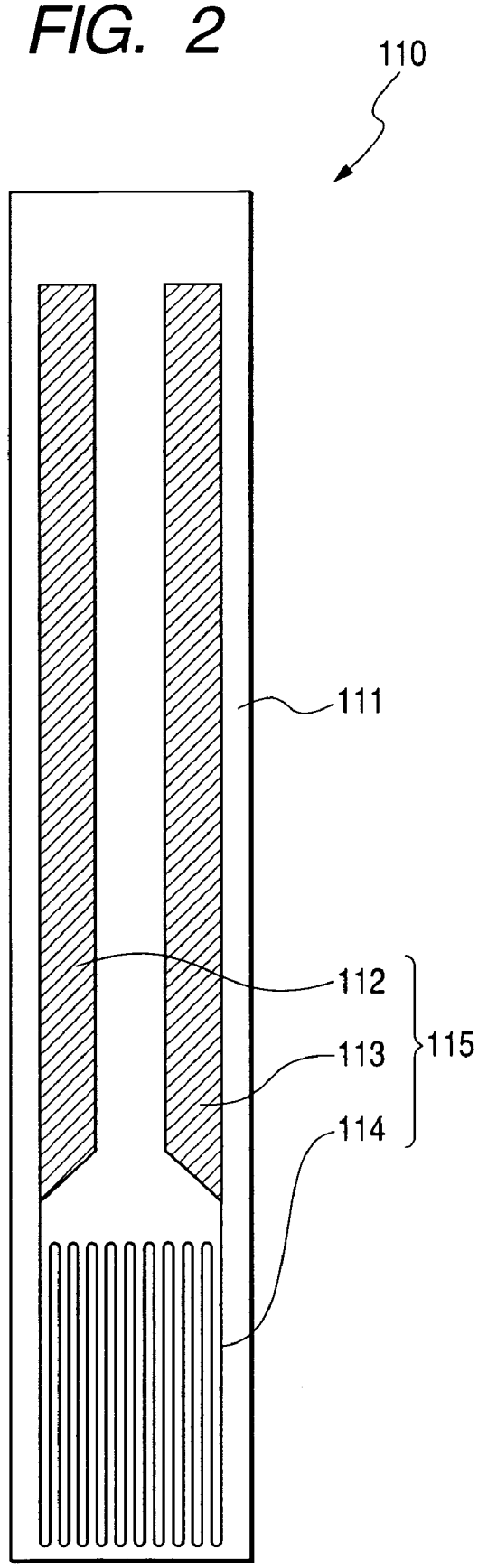
FIG. 2 is a schematic diagram of a heater pattern 115 of a ceramic heater 110.

First, the configuration of an exemplary liquid state detection sensor 100 will be described with reference to FIGS. 1 and 2. FIG. 1 is a partial sectional, longitudinal side view of the liquid state detection sensor 100. FIG. 2 is a schematic diagram of a heater pattern 115 of a ceramic heater 110. In the liquid state detection sensor 100, the longitudinal direction of a level detecting portion 70 (i.e., a capacitor composed of an outer cylinder electrode 10 and an inner electrode 20) is referred to as the direction of an axial line O, the side on which a liquid condition detecting portion 30 is provided is referred to as the tip side, and the side on which a fixing (mounting) portion 40 is provided is referred to as the rear side.

The liquid state detection sensor 100 according to this embodiment is a sensor for detecting the state of a urea aqueous solution that is used for reducing nitrogen oxides (NOx) contained in an exhaust gas of a diesel vehicle, that is, the level (liquid level) of the urea aqueous solution, its temperature, and the concentration of urea as its particular component. As shown in FIG. 1, the liquid state detection sensor 100 comprises a level detecting portion 70 which is composed of the outer cylinder electrode 10 having a cylindrical shape and the cylindrical inner electrode 20 provided inside the outer cylinder electrode 10 so as to extend along the axial line O of the outer cylinder electrode 10, a liquid condition detecting portion 30 provided on the tip side of the inner electrode 20, and a fixing portion 40 which is used for attaching the liquid states detection sensor 100 to a urea solution tank 98 (see FIG. 3).

The outer cylinder electrode 10 is made of a metal material and has a long and narrow cylindrical shape extending along the axial line O. Plural narrow slits 15 are formed in the outer cylinder electrode 10 which together assume a straight line extending along each of three generatrices that are arranged at regular intervals in the circumferential direction of the outer cylinder electrode 10. To prevent loss of a rubber bushing 80 (described below) which is interposed between the outer cylinder electrode 10 and the inner electrode 20, holes 16 are formed in a tip portion 11 of the outer cylinder electrode 10 on the respective generatrices along which the slits 15 are formed. One air vent hole 19 is formed in the outer cylinder electrode 10 at a position that is close to its rear-side proximal portion 12 and off the generatrices along which the slits 15 are formed. The tip portion 11 of the outer cylinder electrode 10 extends, in the axial line O direction, to a position located on the tip side of the holes 16 and thereby surrounds, from outside in the radial direction, the ceramic heater 110 (described below) of the liquid condition detecting portion 30 together with a protector 130 which covers and protects the ceramic heater 110. The very tip (the very bottom in FIG. 1) of the outer cylinder electrode 10 is open, whereby the protector 130 of the liquid condition detecting portion 30 can be seen through the opening.

The proximal portion 12 of the outer cylinder electrode 10 is welded to the outer circumferential surface of an electrode support 41 of the metal fixing portion 40 so as to engage with the latter. The fixing portion 40 functions as a seat for fixing the liquid state detection sensor 100 to the urea solution tank 98, and fixing holes (not shown) through which to insert fixing bolts are formed in a brim 42 of the fixing portion 40. The fixing portion 40 is provided, on the opposite side of the brim 40 to the electrode support 41, with an accommodation portion 43 which accommodates components including a circuit board 60 which is mounted with circuits (described below) for detecting the level, temperature, urea concentration, etc., of a urea aqueous solution, input/output circuits for electrical connection to external circuits (e.g., an engine control unit (ECU) of an automobile; not shown), and other circuits. The outer cylinder electrode 10 is grounded via the fixing portion 40.

The circuit board 60 is mounted on board mounting portions (not shown) that project from the four inner-surfaces-connecting lines of the accommodation portion 43. The accommodation portion 43 is covered with and protected by a cover 45 which is fixed to the brim 42. A connector 62 is fixed to a side wall of the cover 45, and connection terminals (not shown) of the connector 62 are connected to patterns (an input/output circuit section 290 (described below)) on the circuit board 60 via a cable 61. The circuit board 60 and the ECU are connected to each other via the connector 62.

A through-hole 46 is formed in the electrode support 41 of the fixing portion 40 so as to communicate with the space in the accommodation portion 43, and a proximal portion 22 of the inner electrode 20 is inserted through the hole 46. The inner electrode 20 of this embodiment is made of a metal material, has a long and narrow cylindrical shape, and extends along the axial line O. An insulative coating 23 made of a fluorine resin such as PTFE, PFA, or ETFE, an epoxy resin, a polyimide resin, or the like is formed on the outer circumferential surface of the inner electrode 20. The insulative coating 23 is formed as a resin coating layer by applying such a resin to the outer surface of the inner electrode 20 by dipping or electrostatic powder coating and then heat treating. The level detecting portion 70 is composed of the inner electrode 20 and the outer cylinder electrode 10 which form a capacitor whose capacitance varies depending on the level of a urea aqueous solution.

A pipe guide 55 and an inner case 50 both for fixing the inner electrode 20 to the fixing portion 40 are joined to or engaged with the rear-side proximal portion 22 of the inner electrode 20. The pipe guide 55 is an annular guide member that is joined to the end portion of the proximal portion 22 of the inner electrode 20. The inner case 50 is a resin member that is shaped like a cylinder having a brim and serves to position and support the inner electrode 20 so that the inner electrode 20 is reliably insulated from the outer cylinder electrode 10. The tip-side portion of the inner case 50 is engaged with the electrode support 41 of the fixing portion 40. The inner case 50 has a brim 51 which projects outward in the radial direction. To engage the inner case 50 with the electrode support 41, the inner case 50 is inserted into the hole 46 of the electrode support 41 from the side of the accommodation portion 43. The brim 51 comes into contact with the bottom surface of the accommodation portion 43, whereby the inner case 50 is prevented from passing through the hole 46. The inner electrode 20 is inserted into the inner case 50 from the side of the accommodation portion 43. The pipe guide 55 comes into contact with the brim 51 and thereby prevents the inner electrode 20 from coming off the inner case 50.

Further, the outer circumferential surface and the inner circumferential surface of the inner case 50 are provided with respective O-rings 53 and 54. The O-ring 53 seals the gap between the outer circumferential surface of the inner case 50 and the inner circumferential surface of the electrode support 41 of the fixing portion 40, and the O-ring 54 seals the gap between the inner circumferential surface of the inner case 50 and the outer circumferential surface of the proximal portion 22 of the inner electrode 20. With this measure, when the liquid state detection sensor 100 is attached to the urea solution tank 98 (see FIG. 3), the urea solution tank 98 is kept watertight and airtight, that is, the inside and the outside of the urea solution tank 98 are prevented from communicating with one another via the accommodation portion 43. A plate-like sealing member (not shown) is attached to the tip-side surface of the brim 42 of the fixing portion 40, whereby sufficient watertightness and airtightness are secured between the brim 42 and the urea solution tank 98 when the liquid state detection sensor 100 is attached to the urea solution tank 98.

In attaching the inner electrode 20 to the fixing portion 40, the pipe guide 55 is pressed against the brim 51 of the inner case 50 by two pressing plates 56 and 57. The insulative pressing plate 56 is fixed to the fixing portion 40 with screws 58 while pushing the pipe guide 55 with the pressing plate 57 interposed between the pressing plate 56 itself and the pipe guide 55. As a result, the inner electrode 20 which is joined to the pipe guide 55 is fixed to the electrode support 41. The pressing plates 56 and 57 have holes 59 at the centers. Electrode lead wires 52 of the inner electrode 20 and a twin-core cable 91 containing two lead wires 90 (only one of which is shown in FIG. 1) for electrical connection to the ceramic heater 110 (described later) are inserted through the holes 59 and electrically connected to corresponding patterns on the circuit board 60. A ground-side electrode of the circuit board 60 is connected to the fixing portion 40, whereby the outer cylinder electrode 10 which is welded to the fixing portion 40 is electrically connected to the ground side.

In this embodiment, the liquid condition detecting portion 30 which is disposed adjacent to the tip portion 21 of the inner electrode 20 is composed of the ceramic heater 110 as a liquid condition detecting element for detecting the temperature and the urea concentration of a urea aqueous solution, a holder 120 made of an insulative resin and attached to the tip portion 21 of the inner electrode 20, and a protector 130 which covers and protects a portion, exposed from the holder 120, of the ceramic heater 110.

As shown in FIG. 2, the ceramic heater 110 is such that a heater pattern 115 mainly made of Pt is formed on a plate-like ceramic base 111 made of an insulative ceramic and is covered with a counter ceramic base (not shown), that is, the heater pattern 115 is buried. The cross section of the pattern serving as a heating resistor 114 is set smaller than that of the patterns of lead portions 112 and 113 which serve as two electrodes for applying a voltage, whereby heat is generated mainly by the heating resistor 114 when energized. Via conductors (not shown) that are electrically connected to electrode pads formed on the surface of the ceramic base 111 are connected to the ends of the lead portions 112 and 113, respectively, and the electrode pads are electrically connected to two connectors 119 (only one of which is shown in FIG. 1) for a relay to the two lead wires 90, respectively. The ceramic heater 110 corresponds to a "liquid condition detecting element" of the invention.

As shown in FIG. 1, the holder 120 which supports the ceramic heater 110 is shaped like a double cylinder having a step. The ceramic heater 110 whose heating-resistor 114-buried portion (see FIG. 2) is exposed is fixed to the small-diameter tip portion of the holder 120 via fixing members 125 and 126 (adhesives). The large-diameter rear portion of the holder 120 is attached to the tip portion 21 of the inner electrode 20. A sealing ring 140 is interposed between the outer circumferential surface of the inner electrode 20 and the inner circumferential surface of the holder 120, whereby the inner electrode 20 is kept water tight and airtight.

Incidentally, before the holder 120 is attached, the core wires of the two lead wires 90 of the cable 91 are joined to the respective connectors 119 of the ceramic heater 110 by crimping or soldering. Further, the connecting portions of the connectors 119 and the lead wires 90 and nearby portions of the connectors 119 and the lead wires 90 are covered with and protected by an insulative protector 95. The two lead wires 90 are inserted through the cylindrical inner electrode 20 and connected to the circuit board 60.

The protector 130 is a metal protective member shaped like a closed-end cylinder. The opening-side portion of the protector 130 is fitted with the small-diameter portion of the holder 120. Liquid communication holes (not shown) are formed through the circumferential wall of the protector 130, whereby a urea aqueous solution goes into and out of the inside of the protector 130.

The liquid condition detecting portion 30 having the above structure is attached to the tip portion 21 of the inner electrode 20 via the holder 120 and is supported elastically by the rubber bushing 80 in the outer cylinder electrode 10. The rubber bushing 80 has a cylindrical shape, and projections 87 formed on the outer circumferential surface of the rubber bushing 80 are engaged with the respective holes 16 of the outer cylinder electrode 10 and thereby fixed to the outer cylinder electrode 10. The outer circumferential surface and the inner circumferential surface of the rubber bushing 80 are each formed with plural grooves (not shown) that extend parallel with the axial line O. When the liquid state detection sensor 100 is attached to the urea solution tank 98, a urea aqueous solution located on the tip side of the rubber bushing 80 and that located on the rear side of the rubber bushing 80 are exchanged through these grooves. These grooves also serve for removal of bubbles.

Figure 3:
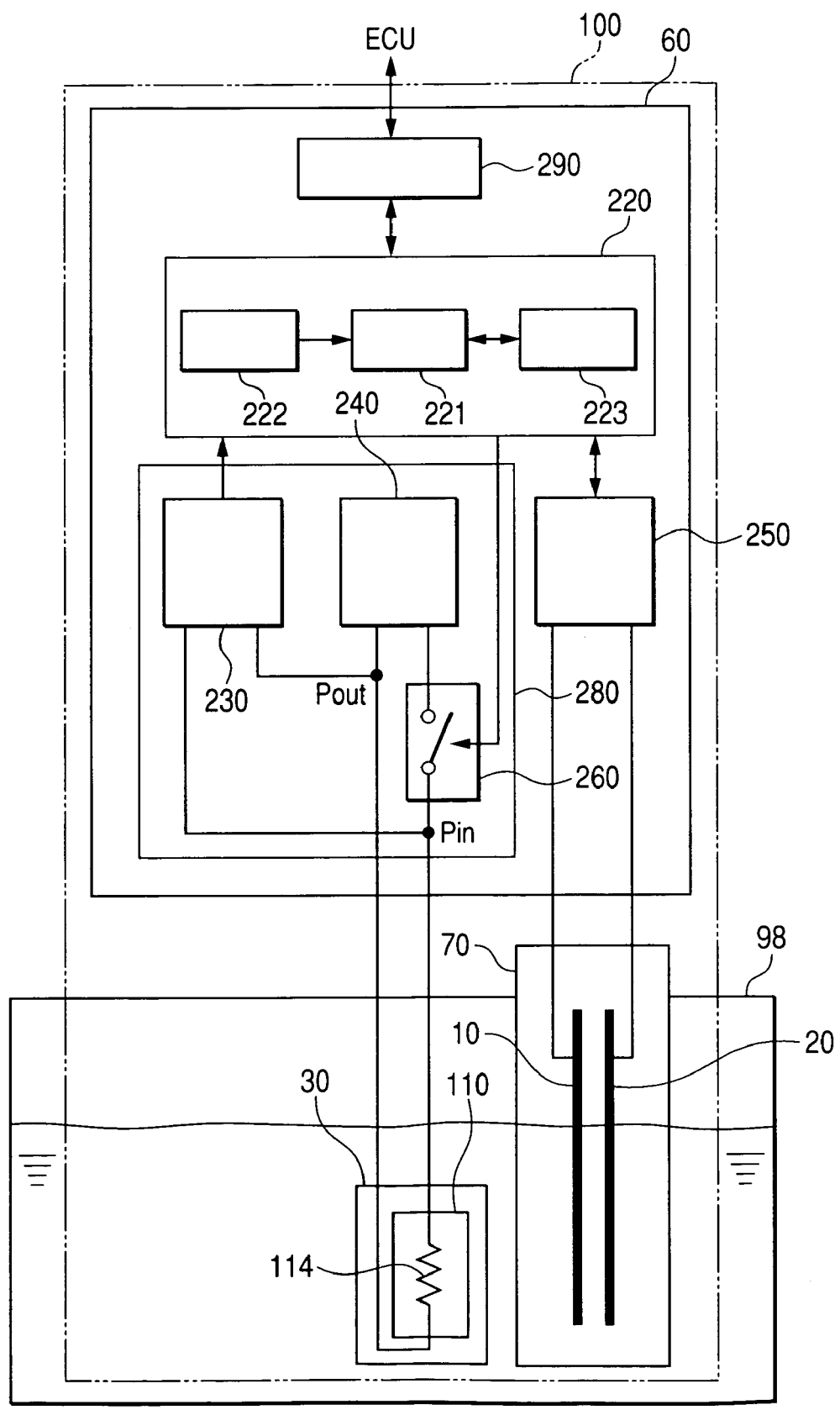
FIG. 3 is a block diagram showing the electrical configuration of the liquid state detection sensor 100.

Next, the electrical configuration of the liquid state detection sensor 100 will be described with reference to FIG. 3. FIG. 3 is a block diagram showing the electrical configuration of the liquid state detection sensor 100.

As shown in FIG. 3, the liquid state detection sensor 100 is attached to the urea solution tank 98 as a liquid container. The level detecting portion 70 having a pair of electrodes (outer cylinder electrode 10 and inner electrode 20) and the liquid condition detecting portion 30 having the ceramic heater 110 in which the heating resistor 114 is buried are immersed in a urea aqueous solution which is the subject of liquid state detection and is contained in the urea solution tank 98. In the liquid state detection sensor 100, a microcomputer 220, a level detecting circuit section 250 for controlling the level detecting portion 70, a liquid condition detecting circuit section 280 for controlling the liquid condition detecting portion 30, and an input/output circuit section 290 for communicating with the ECU are mounted on the circuit board 60. The level detecting circuit section 250, the liquid condition detecting circuit section 280, and the input/output circuit section 290 are connected to the microcomputer 220.

The microcomputer 220 is equipped with a known CPU 221, ROM 222, and RAM 223. The CPU 221 controls the entire liquid state detection sensor 100. The ROM 222 is provided with various storage areas (not shown), and a condition detecting program (described below), Equations (1)-(5) (described below), initial values of various variables, threshold values, etc., are stored in prescribed storage areas of the ROM 222. The RAM 223 is likewise provided with various storage areas, and part of the condition detecting program, values of various variables, timer counts, etc., are temporarily stored in prescribed storage areas of the RAM 223 while the condition detecting program is being run.

The input/output circuit section 290 performs a communication protocol control for input/output of a signal between the liquid state detection sensor 100 and the ECU. The level detecting circuit section 250 is a circuit section which operates according to instructions from the microcomputer 220 to apply an AC voltage between the outer cylinder electrode 10 and the inner electrode 20 of the level detecting section 70, converts a current flowing through the level detecting section 70 (capacitor) into a voltage signal, and outputs the voltage signal to the microcomputer 220.

The liquid condition detecting circuit section 280 is a circuit section which operates according to instructions from the microcomputer 220 to cause a constant current to flow through the ceramic heater 110 of the liquid condition detecting portion 30 and outputs a detection voltage developed across the heat resistor 114 to the microcomputer 220. The liquid condition detecting circuit section 280 is composed of a differential amplifier circuit section 230, a constant current output section 240, and a switch 260.

The constant current output section 240 causes a constant current to flow through the heating resistor 114. The switch 260, which is disposed on a current conduction path to the heating resistor 114, is switched by control of the microcomputer 220. The differential amplifier circuit section 230 outputs, to the microcomputer 220, as a detection voltage, the difference between potentials Pin and Pout appearing at both ends of the heating resistor 114.

Figure 4:
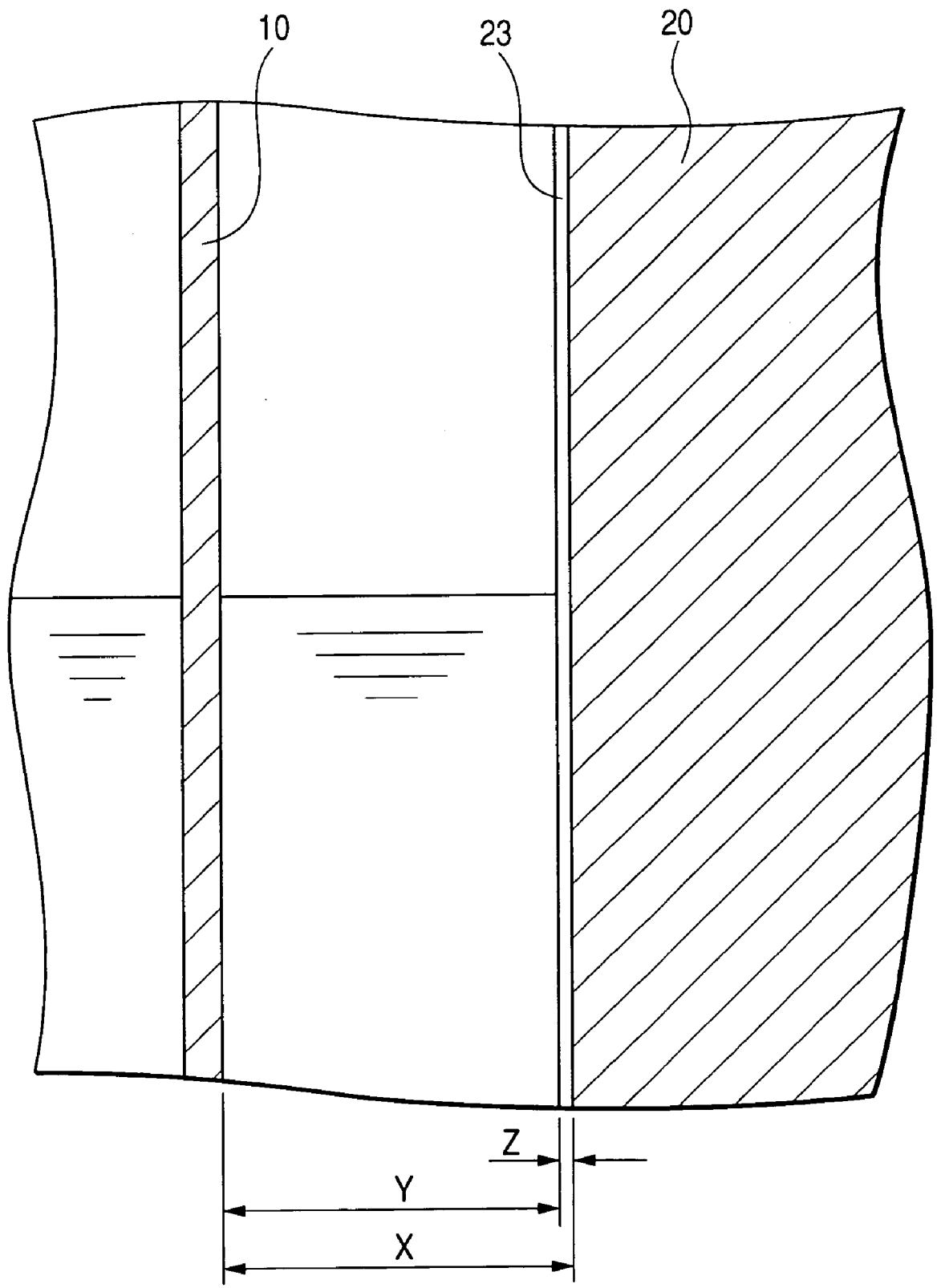
FIG. 4 is an enlarged sectional view of a portion, close to its surface, of a urea aqueous solution that fills up the gap between an outer cylinder electrode 10 and an inner electrode 20.

Next, the principles according to which the liquid state detection sensor 100 according to the embodiment detects the level, temperature, and urea concentration of a urea aqueous solution will be described. First, the principle according to which the level detecting portion 70 detects the level of a urea aqueous solution will be described with reference to FIG. 4. FIG. 4 is an enlarged sectional view of a portion, close to its surface, of a urea aqueous solution that fills up the gap between the outer cylinder electrode 10 and the inner electrode 20.

The liquid state detection sensor 100 (see FIG. 1) is attached to the urea solution tank 98 (see FIG. 3) containing a urea aqueous solution, with the tips of the outer cylinder electrode 10 and the inner electrode 20 opposed to the bottom wall of the urea solution tank 98. That is, the liquid state detection sensor 100 is attached to the urea solution tank 98 such that the axial line O is set parallel with the level variation direction of the urea aqueous solution when its volume in the urea solution tank 98 varies and such that the tips of the outer cylinder electrode 10 and the inner electrode 20 are located on the low level side. The surface level, in the axial line O direction, of the urea aqueous solution existing between the outer cylinder electrode 10 and the inner electrode 20 is detected by measuring the capacitance between the outer cylinder electrode 10 and the inner electrode 20. As is well known, this is based on the fact that the capacitance increases as the radial distance between two concentric cylindrical planes having different potentials decreases.

More specifically, as shown in FIG. 4, in that portion of the gap which is not filled with the urea aqueous solution, the length of a portion across which a voltage difference occurs is equal to a distance X that is the sum of a distance Y that is equal to the thickness of the air layer between the inner circumferential surface of the outer cylinder electrode 10 and the insulative coating 23 and a distance Z that is equal to the thickness of the insulative coating 23. On the other hand, in that portion of the gap which is filled with the urea aqueous solution, the length of a portion across which a voltage difference occurs is equal to the distance Z that is equal to the thickness of the insulative coating 23 because the urea aqueous solution is conductive and hence the potentials of the outer cylinder electrode 10 and the urea aqueous solution are approximately the same.

In other words, the capacitance of that portion of the gap which is not filled with the urea aqueous solution is equal to a composite capacitance of a series connection of a capacitor in which air as a dielectric (insulator) is interposed between electrodes having the distance Y and a capacitor in which the insulative coating 23 as a dielectric is interposed between electrodes having the distance Z. The capacitance of that portion of the gap which is filled with the urea aqueous solution is equal to the capacitance of a capacitor in which the insulative coating 23 as a dielectric is interposed between electrodes having the distance Z. A composite capacitance of a parallel connection of the above two capacitors is measured as a capacitance of the entire level detecting portion 70.

Since the distance Y is much longer than the distance Z, the capacitance per unit area of the capacitor in which air as a dielectric is interposed between electrodes is smaller than that of the capacitor in which the insulative coating 23 as a dielectric is interposed between electrodes. Therefore, the capacitance of the portion of the gap which is filled with the urea aqueous solution varies more than the capacitance of the portion of the gap which is not filled with the urea aqueous solution, and the capacitance of the entire capacitor consisting of the outer cylinder electrode 10 and the inner electrode 20 is proportional to the level of the urea aqueous solution.

The above measurement of the level of the urea aqueous solution is performed by the microcomputer 220 via the level detecting circuit section 250, and a resulting level information signal is output to the ECU (not shown) via the input/output circuit section 290.

Figure 5:
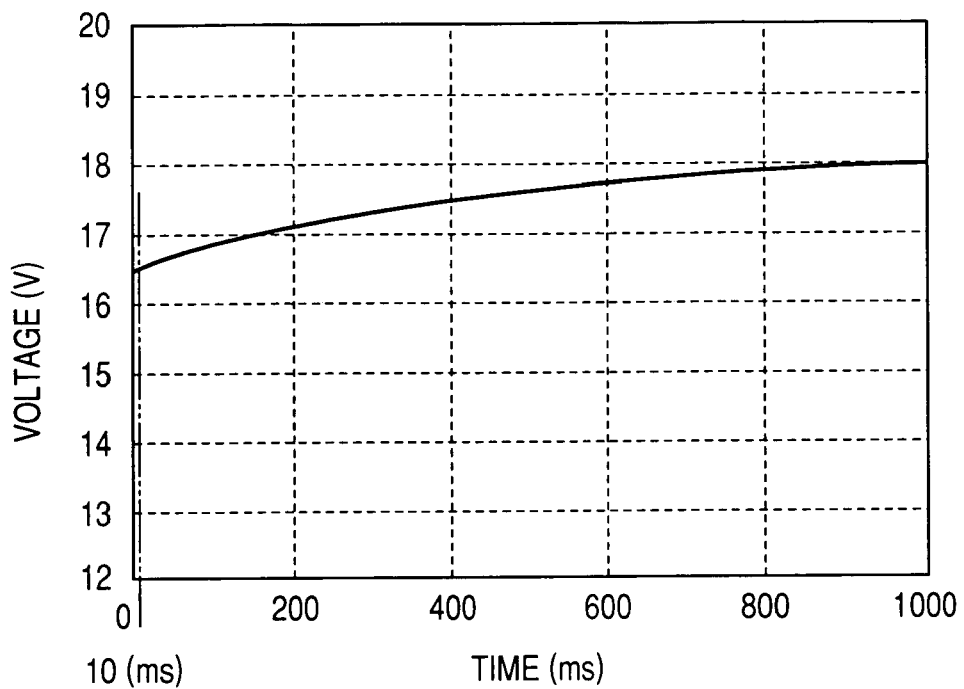
FIG. 5 is a graph showing a voltage corresponding to the resistance of a heating resistor 114 which increases with time from the start of passing a constant current through the heating resistor 114. The temperature of the heating resistor 114 increases accordingly. The graph of FIG. 5 is for an exemplary urea aqueous solution having a urea concentration of 32.5 wt % and a temperature is 25° C.
Figure 6:
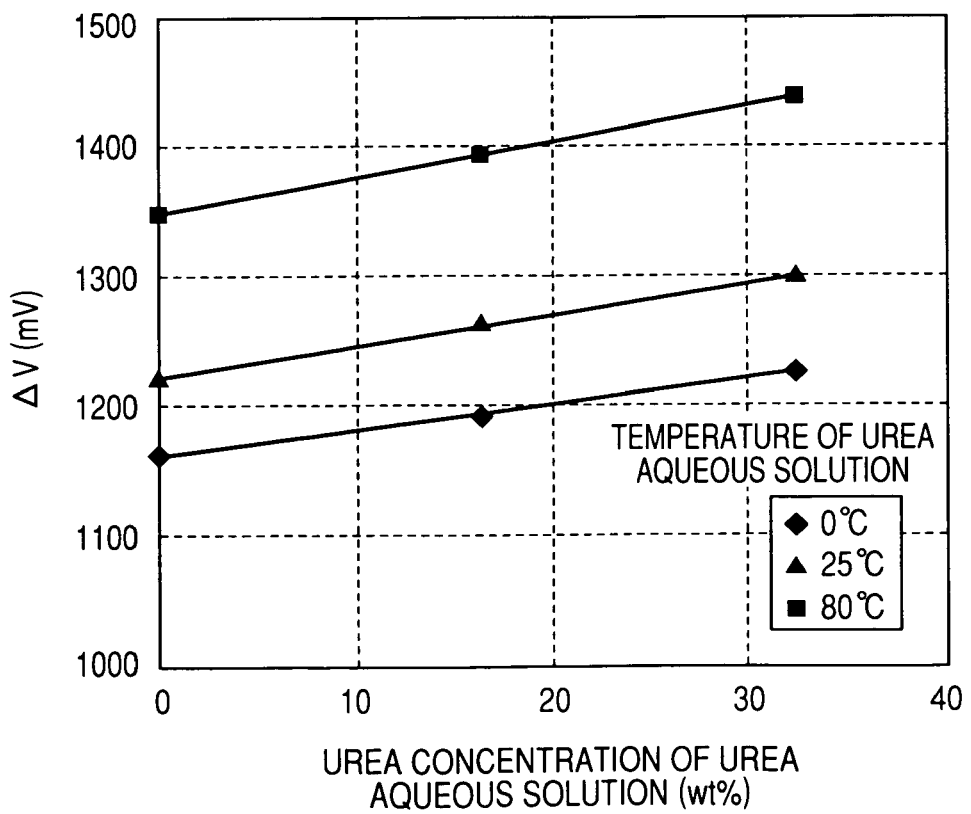
FIG. 6 is a graph showing that the relationship between the voltage variation ΔV of the heating resistor 114 and the urea concentration of a urea aqueous solution is a linear relationship and is also temperature dependent.
Figure 7:
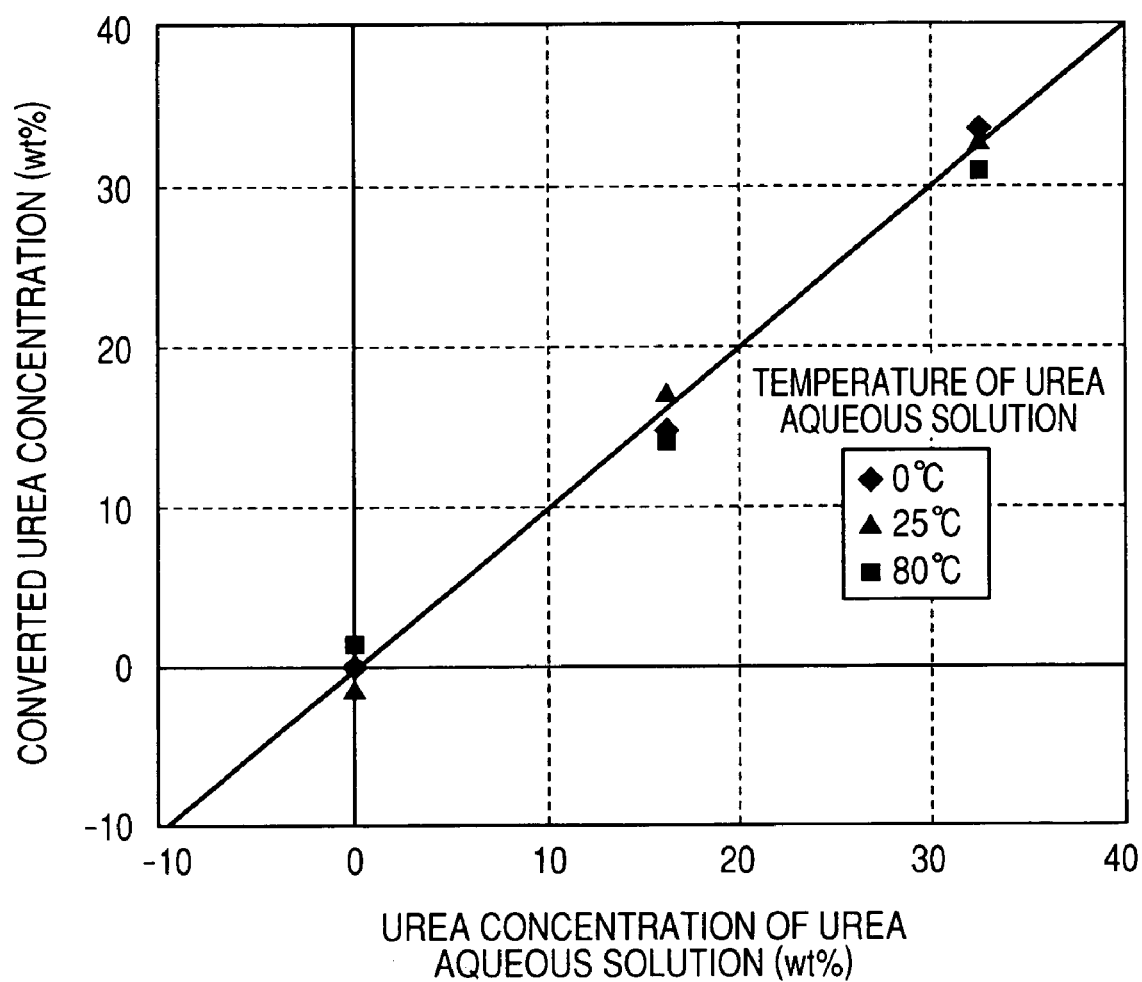
FIG. 7 is a graph showing a corrected (converted) concentration obtained by correcting the relationship between the voltage variation ΔV of the heating resistor 114 and the urea concentration of a urea aqueous solution further taking into account the temperature of the urea aqueous solution so as to approximately coincide with the actual urea concentration.

Next, the principles according to which the temperature of a urea aqueous solution and the concentration of urea as a particular component of the urea aqueous solution are detected by the ceramic heater 110 of the liquid condition detecting portion 30 will be described. FIG. 5 is a graph showing how the voltage corresponding to the resistance of the heating resistor 114 increases as time elapses from the start of an operation causing a constant current to flow through the heating resistor 114. The temperature of the heating resistor 114 increases accordingly, for an exemplary urea aqueous solution whose urea concentration is 32.5 wt % and temperature is 25° C. FIG. 6 is a graph showing that the relationship between the voltage variation ΔV of the heating resistor 114 and the urea concentration of a urea aqueous solution is a linear relationship and is temperature dependent. FIG. 7 is a graph showing a corrected (converted) concentration obtained by correcting the relationship between the voltage variation ΔV of the heating resistor 114 and the urea concentration of a urea aqueous solution further taking into account the temperature of the urea aqueous solution so as to approximately coincide with the actual urea concentration.

Shortly after energization, the temperature of the heating resistor 114 is approximately the same as the temperature of a liquid around the heating resistor 114. This is because the amount of heat thus far generated is small. This is shown in the graph of FIG. 5. The temperature of the heating resistor 114 increases continuously with time after the start of an operation causing a constant current to flow through the heating resistor 114 (after the start of energization, it takes about 10 ms for the current value to become stable).

Therefore, if the relationship between the voltage corresponding to the resistance the heating resistor 114 when 10 ms has elapsed from the start of its energization and the temperature of the portion, around the heating resistor 114, of a urea aqueous solution is obtained in advance, the temperature of the urea aqueous solution can be measured. The relationship between the resistance exhibited by the heating resistor 114 only a short time after the start of energization and the temperature of the portion, around the heating resistor 114, of a urea aqueous solution is given by $$R_T = R_0(1 + \alpha_0 T). \quad (1)$$

The variable $R_T$ is the resistance of the heating resistor 114 at T° C., and the temperature of a liquid around the heating resistor 114 is also T° C. when energization of the heating resistor 114 is started. The parameter $R_0$ is the resistance (Ω) of the heating resistor 114 at 0° C. The coefficient $\alpha_0$ is the temperature coefficient determined at 0° C. and depends on the material of the heating resistor 114. It is therefore seen from Equation (1) that the resistance of the heating resistor 114 is a linear function of the ambient temperature.

From Ohm's law, the relationship $$R_T = V_T/I \quad (2)$$

holds. Since a constant current is caused to flow through the heating resistor 114, the current I (A) is constant. It is therefore understood that the voltage across the heating resistor 114 (in this embodiment, the output voltage (V) of the differential amplifier circuit section 230) is proportional to the resistance $R_T$ (Ω) (see Equation (2)) and is a linear function of the ambient temperature (see Equation (1)).

When energization of the heating resistor 114 continues, the heat generated by the heating resistor 114 is absorbed by the liquid around it and the quantity of heat absorbed by the liquid depends on its thermal conductivity. That is, the temperature increase rate of the heating resistor 114 depends on the thermal conductivity of the liquid around it. Further, it is known that the thermal conductivity of a liquid depends on the concentration of a particular component contained in it. Therefore, when the heating resistor 114 is immersed in a liquid and heats the liquid for a prescribed time, a change in the thermal conductivity of the ambient liquid can be determined and the concentration of a particular component of the liquid can be obtained as long as the resistance variation rate of the heating resistor 114 is known.

This is shown in the graph of FIG. 6. For example, when the heating resistor 114 that is immersed in a urea aqueous solution of 25° C. is energized for 700 ms, the voltage variation corresponding to the resistance variation of the heating resistor 114 is 1,220 mV, 1,262 mV, and 1,298 mV in the case where the urea concentration of the urea aqueous solution is 0 wt %, 16.25 wt %, and 32.5 wt %, respectively. That is, as the urea concentration of the urea aqueous solution increases and its thermal conductivity decreases accordingly, the heat generated by the heating resistor 114 is absorbed less readily and hence the increase in temperature rate increases. As a result, the resistance variation of the heating resistor 114 increases and the corresponding voltage variation (ΔV in FIG. 6) increases.

As described above, the urea concentration of a urea aqueous solution and the resistance variation of the heating resistor 114 (i.e., the voltage variation) has a linear relationship as shown in FIG. 6. The relationship between the urea concentration of the portion, around the heating resistor 114, of a urea aqueous solution and the voltage variation ΔV corresponding to the resistance variation of the heating resistor 114 is given by $$\Delta V = a_T C + b_T. \quad (3)$$

The variable ΔV (mV) is the difference between a voltage corresponding to a resistance that the heating resistor 114 exhibits only a short time after the start of energization and a voltage corresponding to a resistance that the heating resistor 114 exhibits at a time point when a prescribed detection period (e.g., 700 ms) has elapsed from the start of its energization. The variable C is the urea concentration (wt %) of the urea aqueous solution. The coefficient $a_T$ is the slope of the ΔV-C straight line in the case where the temperature of the urea aqueous solution is T° C. The constant $b_T$ is the intercept of the ΔV-C straight line in the case where the temperature of the urea aqueous solution is T° C.

On the other hand, even if urea aqueous solutions are the same in urea concentration, the temperature increase rate of the heating resistor 114 (i.e., the voltage variation ΔV) varies if the urea aqueous solutions are at different temperatures. That is, the temperature increase rate of the heating resistor 114 also depends on the temperature of the urea aqueous solution.

This is also shown in the graph of FIG. 6. For example, if a urea aqueous solution whose urea concentration is 32.5 wt % and temperature is 25° C. is heated by energizing the heating resistor 114 for 700 ms, the voltage variation ΔV corresponding to the resistance variation of the heating resistor 114 is 1,298 mV. On the other hand, if a urea aqueous solution whose urea concentration is the same that as of the above solution and temperature is 80° C. is heated by energizing the heating resistor 114 for 700 ms, the voltage variation ΔV is 1,440 mV. That is, where the urea concentration of the urea aqueous solution is constant, the resistance variation of the heating resistor 114 decreases and the corresponding voltage variation ΔV decreases at an initially lower temperature of the urea aqueous solution.

As shown above, the relationship between the calculated urea concentration and the resistance variation of the heating resistor 114 (the voltage variation ΔV) depends on the initial temperature of the urea aqueous solution. Therefore, a corrected urea concentration can be calculated by correcting (calibrating) Equation (3) to take into account the temperature of the urea aqueous solution that is determined from Equations (1) and (2). The correction for the temperature of the urea aqueous solution is performed according to the following equations:

$$a_T = a_{25} + x(T - 25) \quad (4)$$

$$b_T = b_{25} + y(T - 25) \quad (5)$$

The parameter a25 is the slope of the ΔV-C straight line in the case where the temperature of the urea aqueous solution is 25° C., and x is the temperature correction coefficient of the slope. Likewise, b25 is the intercept of the ΔV-C straight line in the case where the temperature of the urea aqueous solution is 25° C., and y is the temperature correction coefficient of the intercept.

Values suitable for the correction parameters in Equations (3), (4), and (5) were determined by an experiment or the like as $a_{25}=2.3$, $b_{25}=1.223$, x=0.015, and y=2.45. FIG. 7 shows that concentrations (converted concentrations) of urea aqueous solutions obtained by performing corrections using the above values approximately coincide with actual urea concentrations.

Figure 8:
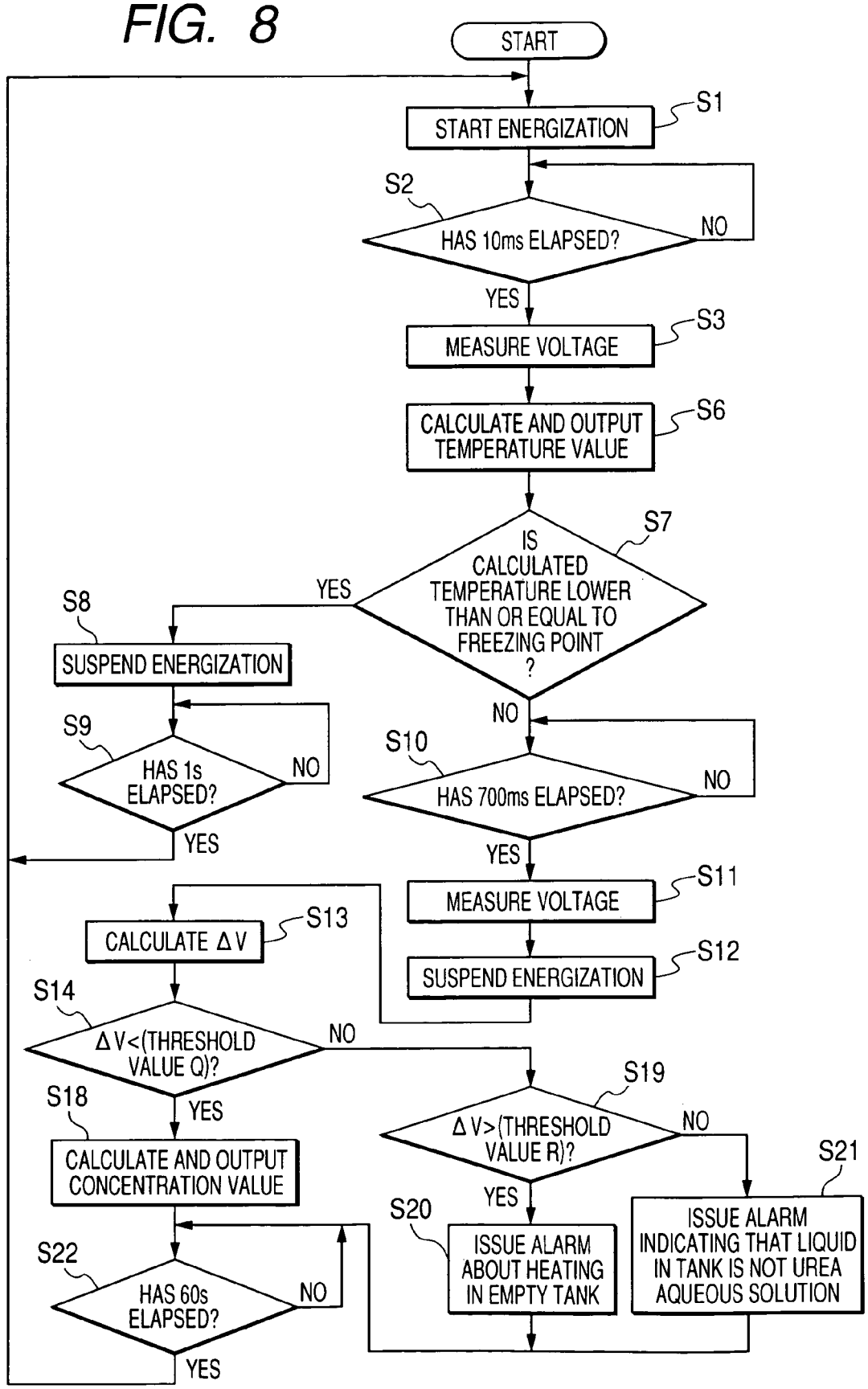
FIG. 8 is a flowchart of a condition detecting program according to an embodiment of the invention.
Figure 9:
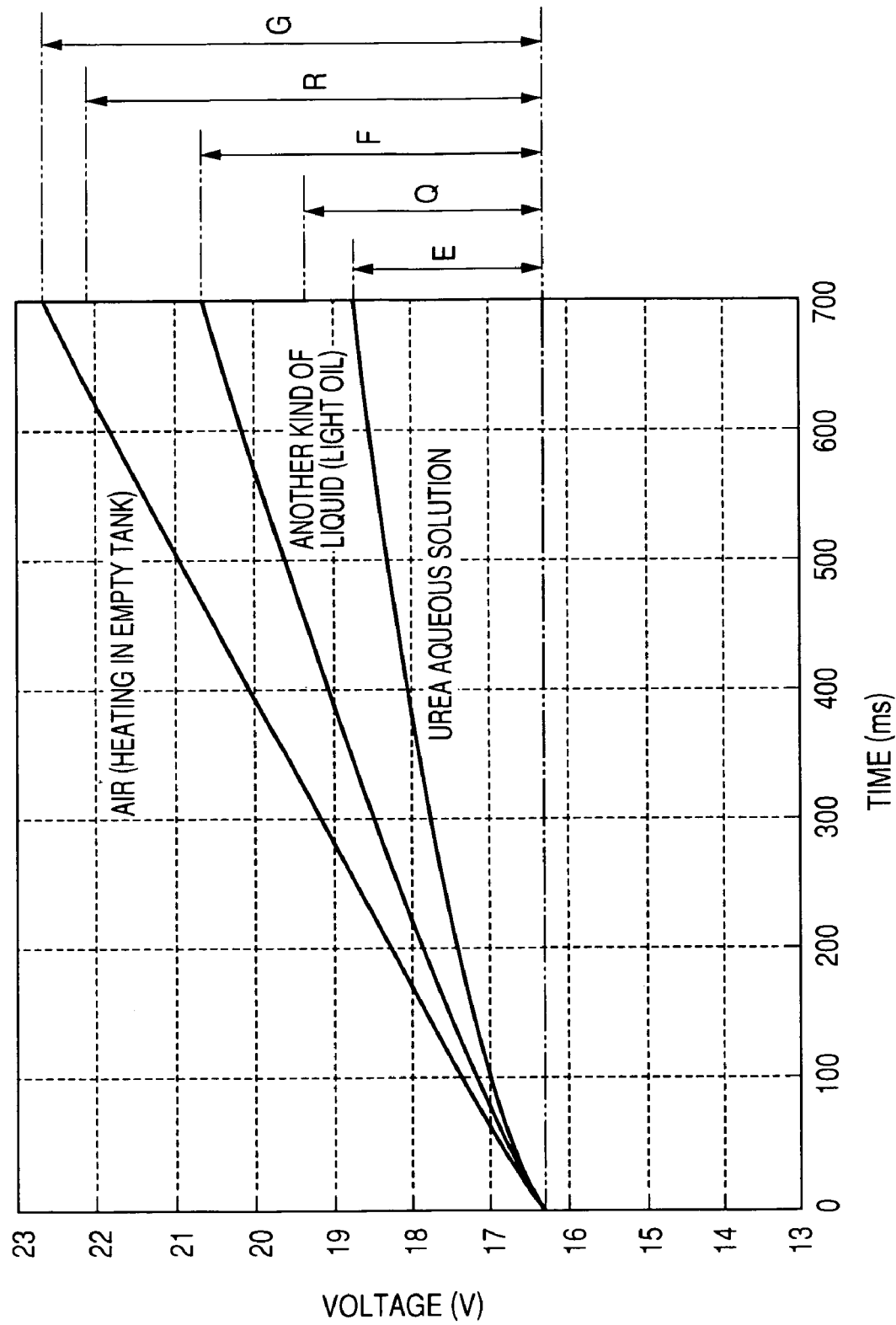
FIG. 9 is a graph illustrating threshold values Q and R which are used for judging whether heating is being performed in an empty tank and whether another kind of liquid is contained in a tank, respectively.

The liquid state detection sensor 100 according to the embodiment detects the level, temperature, and urea concentration of a urea aqueous solution according to the above-described principles. In particular, the temperature and the urea concentration of a urea aqueous solution can be detected by running the condition detecting program stored in the ROM 222 of the microcomputer 220. The condition detecting program will be described below with reference to FIGS. 3, 8, and 9. FIG. 8 is a flowchart of the condition detecting program. FIG. 9 is a graph describing of threshold values Q and R that are used for detecting heating in the urea solution tank 98 if empty, or if another kind of liquid contained in the urea solution tank 98.

To detect the state of a urea aqueous solution in response to an instruction from the ECU, the condition detecting program stored in the ROM 222 is read into a prescribed storage area of the RAM 223 and run. As shown in FIG. 8, when a control signal is sent from the microcomputer 220 to the switch 260 (see FIG. 3), at step S1 the switch 260 is closed and energization of the heating resistor 114 by the constant current output section 240 is started. The program waits until passage of 10 ms from the start of energization by referring to the count of a timer program (not shown) which is being separately run (S2: no). As described above, 10 ms is set as an initial energization time to allow the current value to stabilize. This processing prevents a voltage from being measured at step S3 in the 10 ms period.

After a lapse of 10 ms (S2: yes), the program moves to step S3, where the differential amplifier circuit section 230 measures a voltage value of the heating resistor 114 and the detection voltage value is input to the microcomputer 220. The detection voltage value of the heating resistor 114 measured by the differential amplifier circuit section 230 after the start of energization is a "first corresponding value" of the invention, and the CPU 221 which acquires the detection voltage value is a "first corresponding value acquiring unit" of the invention.

In the microcomputer 220, the received voltage value across the heating resistor 114 is represented by VT and a temperature T of the portion, around the heating resistor 114, of the urea aqueous solution is calculated according to Equations (1) and (2). The calculated temperature T is sent from the input/output circuit section 290 to the ECU as a temperature information signal (S6). The CPU 221 which calculates the temperature T of the urea aqueous solution is a "temperature information acquiring unit" of the invention.

On the other hand, at step S7, the temperature T of the urea aqueous solution is compared with the freezing point (−11° C.) of the urea aqueous solution which is stored in the ROM 222 in advance. If the temperature T is lower than or equal to the freezing point (S7: yes), it is judged that the urea aqueous solution is frozen. A control signal is sent to open the switch 260, and energization of the heating resistor 114 is suspended (S8). Waiting is done until passage of 1 s from the start of suspension of energization by referring to the count of the timer program which is being run separately (not shown) (S9: no). This standby time is set long enough so as to allow the temperature of the heating resistor 114 to become equal to the temperature of the portion of the urea aqueous solution around the heating resistor 114 that has been energized for about 10 ms. After a lapse of 1 s (S9: yes), the program returns to step S1, where the temperature of the heating resistor 114 should be equal to the temperature of the surrounding portion of the urea aqueous solution. The CPU 221 which judges at step S7 whether the temperature T of the urea aqueous solution is lower than or equal to the freezing point is a "freezing judging unit" of the invention, and the CPU 221 which outputs a control signal to the switch 260 at step S8 to suspend the energization of the heating resistor 114 is an "energization suspending unit" of the invention. Further, the CPU 221 which causes waiting at one of steps S9 and S22 which are different in standby time by judging at step S7 whether the temperature T of the urea aqueous solution is lower than or equal to the freezing point is a "standby time selecting unit" of the invention.

While the temperature of the portion, around the heating resistor 114, of the urea aqueous solution is lower than or equal to the freezing point, another portion of the urea aqueous solution that has melted once due to heat generated by the heating resistor 114 may freeze again. The ceramic heater 110 may be damaged by pressure due to freezing expansion. In view of this, the temperature T of the urea aqueous solution is monitored by repeating steps S1-S9. If the temperature T of the urea aqueous solution becomes higher than the freezing point (S7: no), the heating resistor 114 remains energized (S10: no) by referring to the count of the timer program until a time period of 700 ms has elapsed.

Once 700 ms has elapsed from the start of energization of the heating resistor 114 (S10: yes), at step S11 a detection voltage value of the heating resistor 114 measured by the differential amplifier circuit section 230 is input to the microcomputer 220 as was done at step S3. After completing this voltage measurement, at step S12 a control signal is output from the microcomputer 220 to the switch 260 and the energization of the heating resistor 114 is suspended. The detection voltage value of the heating resistor 114 measured by the differential amplifier circuit section 230 at step S11 at the time point when 700 ms has elapsed from the start of energization of the heating resistor 114 is a "second corresponding value" of the invention. The CPU 221 which acquires that voltage value is a "second corresponding value acquiring unit" of the invention. Further, the CPU 221 which causes the constant current output section 240 to start energizing the heating resistor 114 at step S1, causes waiting of 700 ms at step S10, and outputs a control signal to the switch 260 to suspend the energization at step S12 is an "energizing unit" of the invention.

At step S13, a difference ΔV is calculated by subtracting the voltage value of the heating resistor 114 obtained at step S3 from that obtained at step S11 at the time point when 700 ms elapsed. If the calculated difference ΔV is smaller than a maximum voltage variation value (threshold value Q; see FIG. 9) that is determined from a possible urea concentration range of the urea aqueous solution (S 14: yes), the difference ΔV is judged a normal value within a normal difference range and the program moves to step S18. At step S18, a urea concentration C of the urea aqueous solution is calculated according to Equations (3)-(5). The difference (i.e., normal difference) ΔV used in this calculation has a value E, for example, that is smaller than the threshold value Q (see FIG. 9). The calculated urea concentration C is sent from the input/output circuit section 290 to the ECU as a concentration information signal. The CPU 221 which calculates a difference ΔV at step S13 is a "difference calculating unit" of the invention. The CPU 221 which calculates a urea concentration C of the urea aqueous solution at step S18 is a "concentration acquiring unit" of the invention.

Then, waiting is done until passage of 60 s by referring to the count of the timer program (S22: no). This standby time is set as a time that is long enough to allow the temperature of the heating resistor 114 to become equal to the temperature of the portion of the urea aqueous solution around the heating resistor 114 that has been energized for about 700 ms. After a lapse of 60 s (S22: yes), the process of detecting a temperature and a urea concentration of the urea aqueous solution is started again.

On the other hand, if the calculated difference ΔV is judged larger than or equal to the threshold value Q (S 14: no), at step S19 a judgment is made whether the calculated difference ΔV is larger than a minimum voltage variation value (threshold value R; see FIG. 9) that may be obtained when the heating resistor 114 is surrounded by air. If the calculated difference ΔV is larger than the minimum voltage variation value (S19: yes), at step S20 a judgment result "heating in an empty tank" is produced and an alarm signal to that effect is sent to the ECU via the input/output circuit section 290. In this case, the difference ΔV has a value G, for example, that is larger than the threshold value R (see FIG. 9). The CPU 221 which judges that an abnormality has occurred on the basis of the judgment results of steps S14 and S19 and which causes execution of step S20 or S21 is an "abnormality judging unit" of the invention.

Even if the difference ΔV is smaller than or equal to the threshold value R (S19: no), since it is larger than or equal to the threshold value Q, at step S21 the liquid around the heating resistor 114 is judged not to be a urea aqueous solution (e.g., it is light oil) and an alarm signal to that effect is sent to the ECU via the input/output circuit section 290. In this case, the difference ΔV has a value F, for example, that is larger than or equal to the threshold value Q and smaller than or equal to the threshold value R. Whichever alarm is issued, the program moves to step S22 for a waiting time of 60 s. After a lapse of 60 s (S22: yes), the process of detecting a temperature and a urea concentration of the urea aqueous solution is started again.

It goes without saying that various modifications to the above embodiment are possible. For example, although in the condition detecting program according to the above embodiment a temperature of a urea aqueous solution is calculated according to Equations (1) and (2) at step S6 and a urea concentration is calculated according to Equations (3)-(5) at step S18, a temperature and a urea concentration may be determined by referring to tables at steps S6 and S18, respectively, the tables being prepared in advance by an experiment or the like and stored in a prescribed storage area.

The standby times of steps S2, S9, S10, and S22 are examples only and optimum standby times may be set by experiment or the like. The standby times of steps S9 and S22 may be set in accordance with a temperature of a urea aqueous solution detected at step S6. Further, although in the above embodiment a calculated temperature of a urea aqueous solution is compared with the freezing point of the urea aqueous solution at step S7, a voltage value of the heating resistor 114 measured at a time point when 10 ms has elapsed from the start of energization may be compared with a voltage value of the heating resistor 114 determined in advance by an experiment or the like as corresponding to the freezing point (−11° C.).

The circuit board 60 may be provided as a circuit board for relaying outputs of the level detecting portion 70 and the liquid condition detecting portion 30 and connected to external circuits including the microcomputer 220. The level detection and the temperature and concentration detection may be performed under the control of the external circuits.

In the liquid state detection sensor 100 according to the above embodiment, the outer cylinder electrode 10 and the inner electrode 20 are provided and the surface level of a urea aqueous solution is also detected. However, the outer cylinder electrode 10 and the inner electrode 20 need not always be provided. In the liquid state detection sensor 100 according to the above embodiment, the constant current output section 240 is provided in the liquid condition detecting circuit section 280 and a voltage value corresponding to a resistance value of the heating resistor 114 is acquired by causing a constant current to flow through the heating resistor 114. However, for example, a temperature and a concentration of a urea aqueous solution may be detected by providing a constant voltage output section in a liquid condition detecting circuit section and acquiring a current value corresponding to a current flowing through the heating resistor 114 by applying a constant voltage to the heating resistor 114.

Incidentally, the detection voltage of the heating resistor 114 may temporarily have a large or small value if a urea aqueous solution is shaken violently due to vibration or the like of the vehicle. In such a case, the acquired temperature information or concentration information may temporarily have an abnormal value. For example, more accurate temperature information and concentration information can be obtained by storing plural voltage measurement values and acquiring temperature information and concentration information on the basis of their average. A modified version of the condition detecting program capable of producing more accurate temperature information and concentration information will be described below with reference to FIG. 10. The modified version is different from the condition detecting program according to the above embodiment shown in FIG. 8 in the steps of judging whether a liquid is frozen. That is, in the modified version, as described below, whether a liquid is frozen is judged by two sets of steps.

Figure 10:
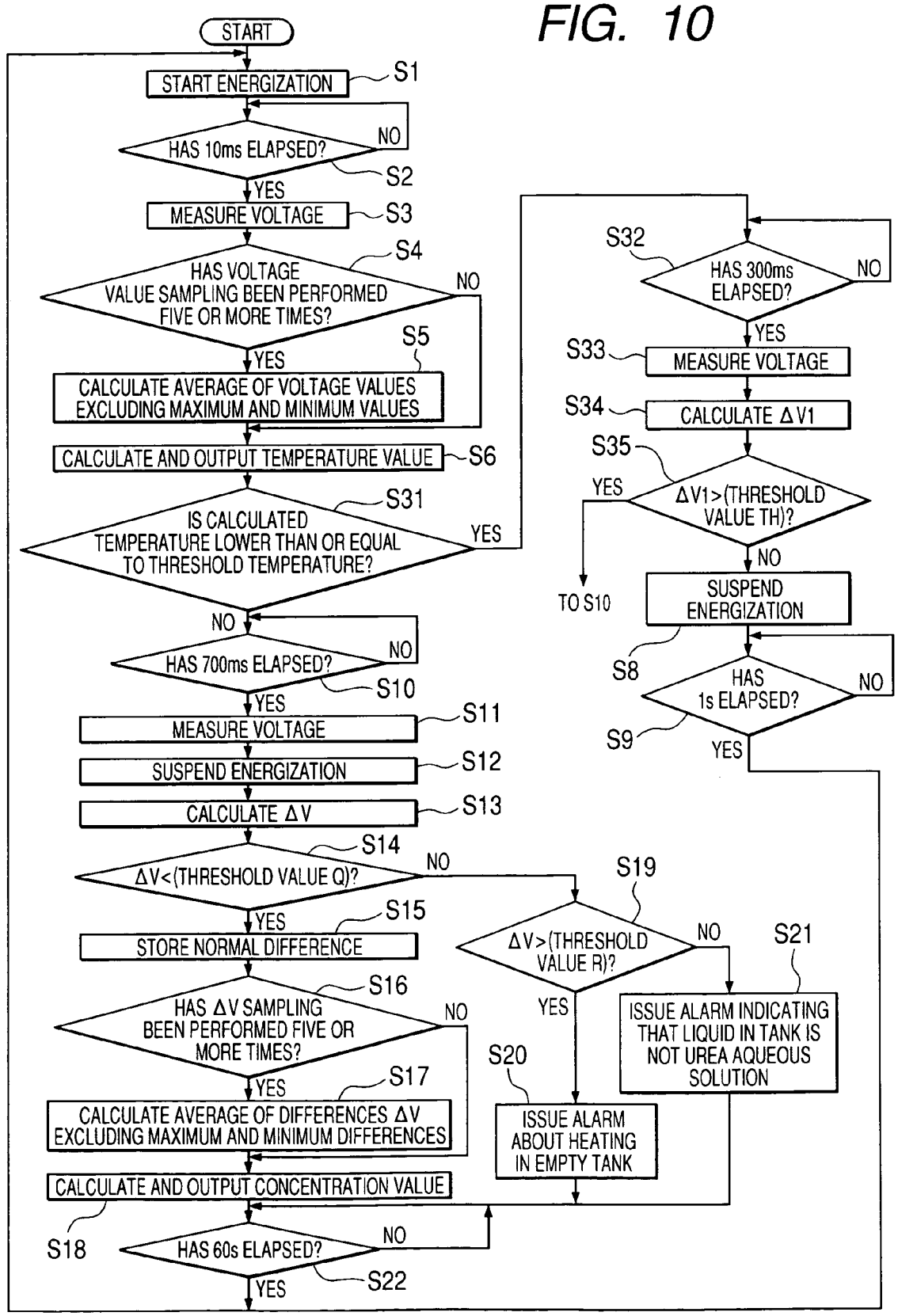
FIG. 10 is a flowchart of a condition detecting program according to a modification.

In a second condition detecting program shown in FIG. 10, steps S4 and S5 are inserted between steps S3 and S6 of the condition detecting program according to the above embodiment and steps S15-S17 are inserted between steps S14 and S18 of the same. Further, in the second condition detecting program, step S7 of the condition detecting program according to the above embodiment is replaced by steps S31-S35. The other steps are the same as in the above embodiment, and hence they are given the same step numbers and will be described in a simplified manner or their description will be omitted.

In the second condition detecting program, as for the detection voltage value of the heating resistor 114 measured at step S3 only a short time after energization and the difference ΔV calculated at step S13, the five most recent values are stored in a prescribed storage area of the RAM 223 by a known memory managing method. Counters for counting the numbers of times of execution of steps S3 and S15, respectively, are stored in prescribed storage areas of the RAM 223. The values of the various variables, counters, etc., that are stored in the RAM 223 so as to be used in running the second condition detecting program are set to initial values (e.g., 0) when the second condition detecting program is started.

As shown in FIG. 10, in the second condition detecting program, when 10 ms has elapsed from the start of energization of the heating resistor 114, a voltage value of the heating resistor 114 is measured and input to the microcomputer 220 (S1-S3). At this time, the detection voltage value is stored in the prescribed storage area of the RAM 223 and the count of the counter for detecting the number of times of execution of step S3 (i.e., the number of times of voltage value sampling) is increased by one.

At step S4, the step S3 execution number counter is queried to determine whether the voltage measurement of step S3 has been performed five or more times after the start of the second condition detecting program. If the voltage measurement has not yet been performed five times (S4: no), the program moves to step S6, where the measured voltage value is converted into a temperature in the same manner as in the above embodiment.

On the other hand, when step S3 is executed 5 or more times as determined in step S4 (S4: yes), the program moves to step S5. Since as mentioned above up to five most recent detection voltage values are stored in the RAM 223, the oldest voltage value is overwritten when step S3 of the second condition detecting program is executed a sixth or greater number of times.

At step S5, an average of three voltage values obtained by excluding maximum and minimum voltage values from the five latest voltage values stored in the prescribed storage area of the RAM 223 as a result of repeated execution of step S3 is calculated. At step S6, a temperature T of the urea aqueous solution is calculated by using the thus-calculated average voltage value.

After the execution of step S6, the program moves to step S31, where the temperature T of the urea aqueous solution calculated at step S6 is compared with a threshold temperature (in this modification, 0°) that is stored in the ROM 222 in advance. If the calculated temperature T is lower than or equal to the threshold temperature (S31: yes), it is judged that the urea aqueous solution is exposed to a cool atmosphere and the program moves to step S32. If the calculated temperature T of the urea aqueous solution is higher than the threshold temperature (S31: no), the urea aqueous solution is judged not to be frozen and the program moves to step S10.

If the program moves to step S32 as a result of an affirmative judgment at step S31, by referring to the count of the timer program, the heating resistor 114 remains energized (S32: no) until a time period of 300 ms has elapsed. Once 300 ms has elapsed from the start of energization of the heating resistor 114 (S32: yes), at step S33 a detection voltage of the heating resistor 114 measured by the differential amplifier circuit section 230 (see FIG. 3) is input to the microcomputer 230 in the same manner as at the above-described step S3. The detection voltage value of the heating resistor 114 that is measured at the time point when 300 ms has elapsed from the start of energization of the heating resistor 114 is a "third corresponding value" of the invention. The CPU 221 which acquires that detection voltage is a "third corresponding value acquiring unit" of the invention.

Then, the program moves to step S34, where an intermediate difference $\Delta V1$ is calculated by subtracting the voltage value of the heating resistor 114 obtained at step S3 from that obtained at step S33 at the time point when 300 ms elapsed from the start of energization. At step S35, it is judged whether the intermediate difference $\Delta V1$ calculated at step S34 is larger than a freezing judgment threshold value TH which was determined in advance by an experiment or the like and is stored in the ROM 222. If the intermediate difference $\Delta V1$ is judged larger than the freezing judgment threshold value TH (S35: yes), the program moves to step S10. If the intermediate difference $\Delta V1$ is judged smaller than or equal to the freezing judgment threshold value TH (S35: no), it is further judged that the urea aqueous solution is frozen. A control signal is sent to the switch 260 to open it, whereby the energization of the heating resistor 114 is suspended (S8). After execution of step S8, the program moves to step S9 and waits for 1 s. After a lapse of 1 s, the program returns to step S1 to start the process of detecting a temperature of the heating resistor 114 once again.

On the other hand, if a negative judgment result is produced at S31 (S31: no) or an affirmative judgment result is produced at step S35 (S35: yes), steps S10-S12 are executed in the same manner as in the above embodiment and the program then moves to step S13. At step S13, a difference $\Delta V$ is calculated by subtracting the voltage value of the heating resistor 114 obtained at step S3 (i.e., the most recent voltage value stored in the RAM 223) from that obtained at step S11. If the calculated difference $\Delta V$ is smaller than the threshold value Q (S14: yes), at step S15 the difference $\Delta V$ is stored in the prescribed storage area of the RAM 223 and the count of the counter for counting the number of times of execution of step S15 (i.e., the number of times the difference $\Delta V$ calculated after voltage sampling is a normal value) is increased by one.

At step S16, the count of the step S15 execution number counter is queried. If the number of times the difference $\Delta V$ is judged normal and stored in the RAM 223 as a normal difference is smaller than five, that is, if step S15 has not been executed five or more times yet (S16: no), the program moves to step S18, where the calculated difference $\Delta V$ is converted into a concentration in the same manner as in the above embodiment.

On the other hand, when step S15 is executed five or more times and it is judged that the sampling of a difference $\Delta V$ (only a normal value) has been performed five times or more (S16: yes), the program moves to step S17. If step S15 is executed a sixth or greater number of times as the execution of the second condition detecting program is continued, the oldest difference $\Delta V$ is overwritten as in the above-described case of voltage values (S3). As a result, five most recent differences $\Delta V$ are always stored in the storage area of the RAM 223.

At step S17, as in the case of step S5, an average of three differences $\Delta V$ obtained by excluding maximum and minimum differences from the five latest differences stored in the prescribed storage area of the RAM 223 as a result of repeated execution of step S13 is calculated. At step S18, the thus-calculated average difference $\Delta V$ is converted into a concentration.

The other steps of the second condition detecting program are the same as the corresponding steps of the condition detecting program according to the above embodiment. Highly accurate temperature information and concentration information can be obtained by calculating, as described above, each of a temperature and a concentration of a urea aqueous solution on the basis of the average of three of five latest detection results. However, the number of times of sampling is not limited to five. Further, the processing which eliminates a maximum value and a minimum value from detection values (detection voltage values or differences $\Delta V$) may be omitted.

As described above, in the second condition detecting program, whether a urea aqueous solution is frozen is judged by two sets of steps, that is, by the step of comparing a temperature T of the urea aqueous solution with the threshold temperature (S31) and the step of comparing an intermediate difference $\Delta V1$ which is acquired in the midst of energization of the heating resistor 114 with the freezing judgment threshold value TH (S35). Therefore, even in the case where the urea concentration of a urea aqueous solution is changed (diluted), this condition detecting program can accurately judge whether the urea aqueous solution is frozen. In the liquid state detection sensor according to this modification, the CPU 221 judges at step S31 whether a temperature T of a urea aqueous solution is lower than or equal to the threshold temperature. If the temperature T is lower than or equal to the threshold temperature, the CPU 221 judges at step S35 whether an intermediate difference ΔV1 is in the prescribed magnitude relationship with the freezing judgment threshold value TH (in this modification, whether the intermediate difference ΔV1 is larger than the freezing judgment threshold value TH). The CPU 221 and associated judgment steps constitutes a "freezing judging unit" of the invention.

The invention can be applied to a liquid state detection sensor capable of detecting the temperature and the concentration of a liquid with a single sensor.

This application is based on Japanese Patent Application JP 2005-200808, filed Jul. 8, 2005, and Japanese Patent Application JP 2005-277776, filed Sep. 26, 2005, the entire contents of which are hereby incorporated by reference, the same as if set forth at length.

What is claimed is:

1. A liquid state detection sensor for detecting the state of a liquid contained in a liquid container, comprising:
   a liquid condition detecting element that is to be placed in the liquid container and having a heating resistor which generates heat when a current is passed therethrough;
   an energizing unit for energizing the heating resistor for a prescribed detection period;
   a first corresponding value acquiring unit for acquiring, in the detection period, a first corresponding value which corresponds to a first resistance value of the heating resistor;
   a temperature information acquiring unit for determining a temperature of the liquid based on the first corresponding value;
   a second corresponding value acquiring unit for acquiring, after a lapse of the detection period, a second corresponding value which corresponds to a second resistance value of the heating resistor;
   a difference calculating unit for determining a difference between the second corresponding value and the first corresponding value; and
   a concentration acquiring unit for determining a concentration of a particular component of the liquid based on the difference between the second and first corresponding values,
   wherein the concentration acquiring unit determines the concentration of a particular component of the liquid based on the difference between the second and first corresponding values and the temperature of the liquid.

2. The liquid state detection sensor as claimed in claim 1, further comprising:
   a freezing judging unit for judging, in the detection period, based on the temperature determined by the temperature information acquiring unit, whether the liquid is frozen; and
   an energization suspending unit for suspending the energization of the heating resistor by the energizing unit when the freezing judging unit judges that the liquid is frozen.

3. The liquid state detection sensor as claimed in claim 2, further comprising a third corresponding value acquiring unit for acquiring a third corresponding value which corresponds to a third resistance value of the heating resistor during the detection period and after acquisition of the first corresponding value,
   wherein the freezing judging unit judges that the liquid is frozen when the determined temperature is lower than or equal to a preset threshold temperature and an intermediate difference between the third corresponding value and the first corresponding value is in a prescribed magnitude relationship with a freezing judgment threshold value.

4. The liquid state detection sensor as claimed in claim 2, wherein:
   the energizing unit resumes energizing the heating resistor when a standby time has elapsed from the time of suspension of the energization of the heating resistor; and
   the liquid state detection sensor further comprises a standby time selecting unit for selecting, as the standby time, a first standby time when the energizing unit has energized the heating resistor for the detection period and a second standby time which is shorter than the first standby time when the energization suspending unit has suspended the energization of the heating resistor.

5. The liquid state detection sensor as claimed in claim 1, wherein:
   the liquid state detection sensor further comprises an abnormality judging unit for judging whether an abnormality has occurred in the liquid container using the difference determined by the difference calculating unit; and
   the concentration acquiring unit determines a concentration of the particular component of the liquid when the abnormality judging unit judges that no abnormality has occurred.

6. The liquid state detection sensor as claimed in claim 1, wherein:
   the energizing unit causes a constant current to flow through the heating resistor; and
   the first corresponding value acquiring unit acquires a voltage value as the first corresponding value and the second corresponding value acquiring unit acquires a voltage value as the second corresponding value.

7. The liquid state detection sensor as claimed in claim 1, wherein the liquid condition detecting element is a ceramic heater comprising a heating resistor buried in a ceramic base.

8. The liquid state detection sensor as claimed in claim 1, wherein the liquid is a urea aqueous solution and the particular component is urea.

* * * * *